(12) United States Patent
Deterre

(10) Patent No.: US 12,201,827 B2
(45) Date of Patent: Jan. 21, 2025

(54) PHOTOSENSITIVE PIXEL STRUCTURE WITH INCREASED LIGHT ABSORPTION AND PHOTOSENSITIVE IMPLANT

(71) Applicant: PIXIUM VISION SA, Paris (FR)

(72) Inventor: Martin Deterre, Paris (FR)

(73) Assignee: PIXIUM VISION SA, Paris (FR)

(*) Notice: Subject to any disclaimer, the term of this patent is extended or adjusted under 35 U.S.C. 154(b) by 0 days.

(21) Appl. No.: 17/537,808

(22) Filed: Nov. 30, 2021

(65) Prior Publication Data
US 2022/0226640 A1    Jul. 21, 2022

Related U.S. Application Data

(63) Continuation of application No. 15/737,865, filed as application No. PCT/EP2016/001073 on Jun. 23, 2016, now Pat. No. 11,197,993.

(30) Foreign Application Priority Data

Jun. 24, 2015 (EP) .................................. 15001873

(51) Int. Cl.
   *A61N 1/05*     (2006.01)
   *A61N 1/36*     (2006.01)
   *H01L 27/146*   (2006.01)

(52) U.S. Cl.
   CPC ....... *A61N 1/0543* (2013.01); *A61N 1/36046* (2013.01); *H01L 27/1461* (2013.01); *H01L 27/14629* (2013.01); *H01L 27/1463* (2013.01)

(58) Field of Classification Search
   CPC .... A61N 1/0543; A61N 1/36046; A61N 5/06; A61N 5/0601; A61N 2005/0651; H01L 27/1461; H01L 27/14629; H01L 27/1463
   See application file for complete search history.

(56) References Cited

U.S. PATENT DOCUMENTS

| 5,753,937 A | 5/1998 | Shimomaki et al. |
| 2005/0131490 A1 | 6/2005 | Palanker |
| 2006/0069416 A1 | 3/2006 | Nisch et al. |
| 2010/0096718 A1 | 4/2010 | Hynecek et al. |

(Continued)

FOREIGN PATENT DOCUMENTS

| CN | 1431921 A | 7/2003 |
| CN | 101317128 A | 12/2008 |

(Continued)

OTHER PUBLICATIONS

Boinagrov et al., "Photovoltaic Pixels for Neural Stimulation: Circuit Models and Performance", IEEE Transactions on biomedical circuits and systems, vol. 10, No. 1, Feb. 2016, pp. 85-97.

(Continued)

*Primary Examiner* — Tammie K Marlen
(74) *Attorney, Agent, or Firm* — Workman Nydegger

(57) ABSTRACT

The present invention refers to a photosensitive pixel structure comprising a substrate with a front surface and a back surface, wherein at least one photosensitive diode is provided on one of the surfaces of the substrate. A first material layer is provided at least partially on the back surface of the substrate, wherein the material layer comprises a reflective layer, in order to increase a reflectivity at the back surface of the substrate. Further, the present invention refers to an array and an implant comprising such a photosensitive pixel structure, as well as to a method to produce the pixel structure.

18 Claims, 6 Drawing Sheets

(56) References Cited

U.S. PATENT DOCUMENTS

| | | |
|---|---|---|
| 2010/0262208 A1 | 10/2010 | Parker |
| 2012/0109292 A1 | 5/2012 | Barbosa |
| 2012/0109296 A1 | 5/2012 | Fan |
| 2012/0153423 A1 | 6/2012 | Lee |
| 2013/0015502 A1 | 1/2013 | Fox et al. |
| 2014/0111088 A1 | 4/2014 | Shim |
| 2017/0070180 A1 | 3/2017 | Mills |
| 2018/0064929 A1 | 3/2018 | Deterre |
| 2018/0151607 A1 | 5/2018 | Deterre |
| 2018/0182788 A1 | 6/2018 | Deterre |
| 2020/0251507 A1 | 8/2020 | Deterre |

FOREIGN PATENT DOCUMENTS

| | | |
|---|---|---|
| CN | 102222450 A | 10/2011 |
| CN | 103260560 A | 8/2013 |
| CN | 103681701 A | 3/2014 |
| EP | 2361440 B1 | 11/2013 |
| EP | 2632388 B1 | 3/2020 |
| JP | 62-172765 A | 7/1987 |
| JP | 2006-054252 A | 2/2006 |
| JP | 2006-517435 A | 7/2006 |
| JP | 2012-506623 A | 3/2012 |
| JP | 2014-503229 A | 2/2014 |
| WO | 2004/067088 A1 | 8/2004 |
| WO | 2008/050726 A1 | 5/2008 |
| WO | 2010/048291 A1 | 4/2010 |
| WO | 2012/058477 A2 | 5/2012 |
| WO | 2013/142815 A1 | 9/2013 |

OTHER PUBLICATIONS

International Search Report and Written Opinion for PCT/EP2016/000690 mailed Jul. 29, 2016.

International Search Report and Written Opinion for PCT/EP2016/000776 mailed Aug. 22, 2016.

International Search Report and Written Opinion for PCT/EP2016/001545 mailed Jan. 3, 2017.

International Search Report/Written Opinion received for U.S. Patent Application No. PCT/EP2016/001073, mailed on Sep. 5, 2016.

Lorach et al, "Photovoltaic restoration of sight with high visual acuity", Nature Medicine, vol. 21, No. 5, May 2015, pp. 476-485.

Loudin et al., "Photodiode Circuits for Retinal Prostheses", IEEE transactions on biomedical circuits and systems, vol. 5, No. 5, Oct. 2011, pp. 468-480.

Mandel et al., "Cortical responses elicited by photovoltaic subretinal prostheses exhibit similarities to visually evoked potentials", Nature Communications, 4:1980, DOI: 10.1038/ncomms2980, pp. 1-9.

Wang Lele et al, "Photovoltaic retinal prosthesis: implant fabrication and performance", Journal of Neural Engineering, Jul. 12, 2012, pp. 1-11, vol. 9, No. 4, Institute of Physics Publishing, Bristol, GB.

PHOTOSENSITIVE PIXEL STRUCTURE WITH INCREASED LIGHT ABSORPTION AND PHOTOSENSITIVE IMPLANT

CROSS-REFERENCE TO RELATED APPLICATIONS

The present application is a continuation of U.S. patent application Ser. No. 15/737,865, filed Dec. 19, 2017, now U.S. Pat. No. 11,197,993, which is a 371 National Stage Entry of International Patent Application No. PCT/EP2016/001073, filed Jun. 23, 2016, which claims the benefit of and priority to EP patent application Ser. No. 15/001,873.7, filed Jun. 24, 2015. The disclosures of the above-identified patent applications are incorporated by reference herein in their entireties.

BACKGROUND OF THE INVENTION

1. Field of the Invention

The present invention relates to a photosensitive pixel structure and a photosensitive implant with such a pixel structure.

2. Description of Related Art

Implant systems are known, which help to restore at least a fraction of vision to patients who have lost sight, for instance through degenerative diseases such as retinitis pigmentosa. Vision may at least to a certain degree be restored with an implant by exploiting the fact that although parts of the retinal tissue have degenerated most of the retina remains intact and may still be stimulated directly by light dependent electrical stimuli. This electrical stimulation can be provided by means of an implant system. Such a system typically comprises special goggles, which are placed in front of an eye of a patient and an implant, in particular a sub-retinal implant, which comprises a plurality of electrodes, which contact living tissue or cells.

In the goggles, typically a camera is provided. The camera is adapted to capture a scene in front of the patient. This captured scene may be translated from visual information into a predetermined IR light pulse signal. The implant in such a case is adapted to receive those IR light pulses and, in response, photosensitive areas on the implant are stimulated based on the scene content received by the camera. The implant then converts the received light into electrical current that may stimulate the residual cells in the retina.

For that purpose, the implants comprise one or more pixel arrays, wherein each individual pixel comprises one or more diode areas, a stimulating electrode and, possibly, a counter electrode.

If a light pulse is directed to a pixel or rather to a photosensitive area of a pixel, a fraction of the photons of that light pulse will be absorbed in the substrate and electron-hole pairs are generated by the photoelectrical effect within the substrate. These electron-hole pairs migrate to respective poles of the pixel structure and an electrical charge may be generated on an electrode by the corresponding photodiode circuit in response thereto. Consequently, the more photons are absorbed in the substrate, the higher may the charge be, which is generated by the pixel structure. The absorption or absorption rate for photons may depend on the wavelength of the incident light, material properties, incidence area, i.e. photoactive area, and the thickness of the absorbing substrate. In order to increase the absorption of incident light, and thus ultimately increase the charge generation in the pixel structure, the thickness of the substrate may be increased. However, it is not always desired to increase the thickness of a substrate.

For instance, implants are known for neural stimulation comprising such photosensitive pixel structures or arrays. In such implants, in order to reliably stimulate residual cells, the current density, i.e., the charge delivered per phase per electromagnetic pulse, e.g. per light pulse, in particular IR pulse, in a predetermined time, should be as high as possible in order to sufficiently stimulate residual cells. At the same time, the implants shall be kept as small as possible for minimal invasivity. As such, ideally, an implant has a thickness of less than 100 µm, ideally less than 50 µm, and preferably of 30 µm or less. Thin implants further allow a facilitated fabrication, in particular regarding structures, which shall extend through the entire thickness of the implant.

Likewise, in order to increase the resolution of a photosensitive array, the size of individual pixels, i.e., the surface area required by each pixel in order to detect sufficient light for charge generation, desirably shall be reduced. That may be applicable for implants as well as other photosensitive structure, such as photosensitive chips in cameras, detection devices and others.

BRIEF SUMMARY OF THE INVENTION

It is therefore an object of the present invention to omit at least one of the problems of the prior art. In particular, it is an object of the invention to provide an enhanced pixel structure. Desirably, the absorption for incident light shall be increased. Further, it may be an object to provide a photosensitive pixel structure with decreased size. Further it may be an object of the invention to provide a pixel array or an implant with an increased resolution.

The problem is solved according to the invention with a pixel structure, a pixel array, an implant, and a method. Advantageous developments are subject to the dependent claims.

According to an aspect of the present invention, a photosensitive pixel structure is provided, which comprises a substrate with a front surface and a back surface. At least one photosensitive diode or a photosensitive area is provided on one of the surfaces of the substrate. Further, a first material layer is provided at least partially on the back surface of the substrate, wherein that material layer comprises a reflective layer. It will be noted that the reflective layer may also be an integral part of the substrate, for instance by doping or thermally growing structures on the surface of the substrate itself. The reflective layer or the first material layer may also be provided as separate layer on the surface of the substrate, for instance deposited by methods known from the art such as electrochemical deposition, vacuum deposition or others.

It will be understood that any material, which may alter, and in particular increase, the reflectivity of light transmitted through the substrate and incident on an interface between the substrate and the first material layer, i.e., the back surface of the substrate may be considered a "reflective material" or a "reflective layer" in the context of the present invention. Reflectivity values of such a reflectivity layer may be compared to the reflectivity inherent to the substrate material alone. Notably, reflectivity values provided herein refer to reflectivity with normal incidence, i.e., an incidence angle perpendicular to the respective surface. Such materials suitable to be used as a reflective material in the first material layer may for instance comprise aluminium, titanium, platinum and/or palladium or alloys thereof, such as, e.g. a titanium-nickel alloy, also known as nitinol, or others. Further materials that may provide increased reflectivity may be ceramic layers, such as aluminium oxide, silicon carbide or others, which may also provide a hermetic sealing and/or biocompatible characteristics suitable for an implant. In order to achieve such properties, the thickness of the respective layers may have to be varied, e.g. increased, in order to provide a hermetic coating.

A "front surface" shall describe a surface onto which or through which incident light is applied, which is then transmitted from outside of the substrate into the substrate. Accordingly, a "back surface" is a surface of the substrate or any respective layer, which is on an opposite side of the substrate compared to the "front surface". Thus, the "back surface" of the substrate characterizes a surface to which the light incident on the front surface and transmitted through the substrate is incident from within the substrate.

By providing a reflective layer or a reflective structure, e.g. a layer-like structure within the substrate or on the back surface of the substrate, the portion of the light, which is not absorbed when being transmitted through the substrate from the front surface of the substrate may, at least partially, be reflected back into the substrate. That way, an increased portion of the originally incident light on the front surface of the substrate may be absorbed. Thus, a higher charge may be generated by the pixel structure while, at the same time, not or negligibly thickening the substrate or the pixel structure as a whole.

According to a development of the present invention, the substrate of the photosensitive pixel structure may comprise a material, which is adapted to absorb light of a predetermined wavelength, or a predetermined wavelength range, or various predetermined wavelengths or wavelength ranges. In particular, the substrate may comprise silicon. In particular, the substrate may be adapted to absorb infrared light, preferably infrared light of the near-infrared range, specifically infrared light within the range of about 780 to 1000 nm, in particular a wavelength between about 830 to 915 nm. As an alternative material for the substrate, germanium may be used.

It will be noted that the light absorption for specific wavelengths may be an intrinsic characteristic of the material, such as, for instance, in the case of silicon.

The reflective layer on the back surface of the substrate, i.e. the reflective layer of the material layer, may comprise a layer of buried oxide (BOX). That buried oxide layer may preferably be $SiO_2$. It may, however, also be a different type commonly referred to as silicon-on-insulators (SOI). A BOX-layer may be advantageous, as that layer, during fabrication, may act as an edge stop when the substrate is thinned and edged to its terminal thickness. Further, a BOX-layer which typically is thermally grown from the top silicon layer or substrate may increase the photodiode efficiency, as on an $Si/SiO_2$ interface the surface recombination of minority carriers is reduced. The BOX-layer may be provided by deposition methods, as well. Further, the reflective layer may comprise a layer of aluminium or a layer of titanium. Again, those layers may be separate layers or may be integrated into the substrate layer during production.

In some embodiments of the present invention, the first material layer comprises a layer of buried oxide, preferably $SiO_2$, and a layer of aluminium. In such embodiments, the layer of buried oxide may be sandwiched between the substrate and the aluminium layer. By combining the BOX-layer and the aluminium layer, the reflectivity from the back surface of the substrate, where the material layer is provided, may be increased even above the sum of the individual material layers.

It could be experimentally shown that the reflectivity of the back surface being defined by silicon only, is about 21%. Further, experimental results could show that by providing a titanium layer, the reflectivity from the back surface may be between 20-22% and the provision of a BOX-layer resulted in reflectivity values from the back surface of between 16 to 21%. It needs, however, to be noted that by providing a titanium layer, the pixel structure could already be provided with a hermetic coating which is biocompatible. The BOX-layer itself may easily be fabricated and may increase the photodiode efficiency. Thus, even the provision of an additional material layer, which does not immediately increase the reflectivity from a back surface of the substrate, may provide advantages within the scope of the present invention.

By providing an aluminium layer alone as the first material layer, i.e. here the reflective layer, on the back surface of the substrate, reflectivity from the back surface of the substrate could be increased to about 64%. While an aluminium layer alone, without any further hermetic or biocompatible coating may not immediately be suitable for an implant structure, according to some embodiments of the present invention, a photosensitive structure such as a photo detector, a light-sensitive chip for a camera or similar, may be provided. The present invention is therefore not restricted to photosensitive implants.

According to other embodiments of the present invention, at least on a surface of the first material layer facing away from the substrate, a second material layer is provided. That second material layer may hermetically cover at least the first material layer and/or the back surface of the substrate. The material properties of the second material layer may, generally, be the same as set out above for the first material layer.

In particular embodiments, the second material layer may be a titanium layer. That titanium layer may be provided on a surface of the material layer made of aluminium or BOX. That way, the advantages of the individual layers may be combined. As such, a combination of a BOX-layer and a titanium layer may provide a hermetic and biocompatible pixel structure with a reflectivity on the back surface of the substrate of up to 73%.

In specific embodiment of the present invention, a BOX-layer and an aluminium layer are provided, wherein the BOX-layer is sandwiched between the substrate and the aluminium layer. That layer of buried oxide may preferably consist of or at least comprise $SiO_2$. Such embodiments allow an increase of reflectivity from the back surface of the substrate of up to 92.5%. The titanium layer may be provided as a part of the first material layer or as the second material layer.

The second material layer consequently may comprise or consist of titanium and/or further materials, in particular metals. These may allow a hermetic sealing of the at least back surface of the pixel structure and/or further increase the reflectivity at the back surface of the substrate. In some embodiments, multiple layers of a material, such as multiple titanium layers, may be provided in the first and/or second material layer. Accordingly, the second material layer may for instance comprise to layers of titanium, which were deposited subsequent to another.

In some embodiments of the present invention, the first and/or second material layer comprises titanium, wherein that titanium layer has a thickness of not less than 100 nm, preferably a thickness of more than 200 nm and most preferably a thickness of 500 nm or, possibly, more. Such a titanium layer, which is provided advantageously as the outer most layer of the pixel structure, may provide a hermetic sealing and, at the same time, may provide a biocompatible cover. That way, it may be enabled to use a pixel structure according to the present invention in an implantable pixel array for instance in a highly corrosive region of a body, such as the vitreous body of an eye.

Notably, the higher the thickness of the titanium layer the higher the hermetic sealing of the surface or the entire structure. That way, a sufficient hermetic sealing may be provided and the titanium of the stack layer of such embodiments has a sufficient thickness to maximize the reflectivity at the back surface of the substrate.

In some embodiments according to the invention, when an aluminium layer is used as additional layer in the first material layer or the second material layer, the aluminium layer preferably has a thickness of more than 50 nm, more preferably a thickness of more than about 60 nm. In particular, the aluminium layer may be chosen to be 100 nm or more.

Advantageously, the first material layer preferably comprises a buried oxide layer. That buried oxide layer may have a thickness which is adapted to the characteristics and/or the thickness of the further materials used. As such, in a case that a stack of titanium and buried oxide layer is used as a first material layer, the thickness of the buried oxide layer preferably is in the range of about 65 nm to 210 nm. In a case that a stack of aluminium and buried oxide layer is used as a first material layer, the thickness of the buried oxide layer preferably is in the range of about 90 nm to 170 nm. Most preferably, the thickness of the buried oxide layer has a thickness of about 130 nm or 430 nm or 130 nm plus any multiple of 300 nm.

By varying the thickness of the buried oxide layer depending on the further materials used in the first and/or second material layer, the reflectivity of the material layer or material layers on the back surface of the substrate may be increased and, ideally, maximized.

Again, it is to be noted that the layer thickness of the buried oxide layer may be varied around the preferred thickness of 130 nm, 430 nm, or 130 nm plus any multiple of 300 nm, as indicated above. The reflectivity of the first material layer varies periodically with a change of the thickness of the buried oxide layer on the back surface of the substrate. The period of that variation is about 300 nm. In order to, ideally, maximize the reflectivity, the targeted value, for instance the value of the first reflectivity peak at about 130 nm layer thickness of buried oxide, shall be approached as close as possible.

However, due to the fabrication process, control of the thickness of the buried oxide layer within a tight window around the reflectivity peaks is challenging. Therefore, materials in the stack of the first material layer adjacent to the buried oxide layer are advantageous, which yield a preferably flat slope in reflectivity with varying thicknesses of the buried oxide layer. As such, the use of aluminium may be preferred over titanium as reflective layer adjacent to the buried oxide layer in the first material layer. A maximum reflectivity of the radiation incident on the back surface of the substrate in this case is about 92.5%. In a thickness range of between about 65 nm to 210 nm buried oxide, the reflectivity of a stack of buried oxide and aluminium is equal to or above 95% of that maximum reflectivity. Accordingly, in such a configuration, about 90%, or more of the incident light may be reflected at the back side of the substrate.

In contrast, in a stack of buried oxide with titanium, a maximum reflectivity of such a buried oxide/titanium stack is about 72% of the radiation incident on the back surface of the substrate. The buried oxide layer thickness may be varied within a range of between about 90 and 170 nm, if the reflectivity should be at least 95% or more of the maximum reflectivity. That thickness range is narrower than in the case for a buried oxide/aluminium stack, thus requiring better control of the production parameters. The. In such a configuration, about 70% or more of the incident light may be reflected at the back side of the substrate. Notably, the reflectivity value in the examples provided above refers to an angle of incidence of light on the surface of 90°, i.e., normal incidence.

A preferred embodiment of the present invention comprises a BOX-layer with a titanium layer as the first material layer. That way, a pixel structure is provided, which has an increased reflectivity, while, at the same time, being hermetically sealed with a biocompatible coating. Most preferably, between the BOX-layer and the titanium layer, an aluminium layer is provided. That allows to increase the reflectivity at the back surface of the substrate more, while, again, providing a hermetic and biocompatible coating by means of the second material layer, which comprises titanium.

If hermeticity is not desired, a BOX-layer may be stacked with an aluminium layer, only. That allows an increased reflectivity at the back surface of the substrate, which may be advantageously deployed in various applications, such as camera chips, sensors and other detection elements.

According to another aspect of the present invention, a pixel array is provided, wherein the pixel array comprises a plurality of photosensitive pixel structures according to the first aspect of the present invention, wherein the pixel structures are arranged in an array. By providing a pixel array, a plurality of individual, light-sensitive pixel structures may be interconnected. That way, the information, which may be received or collected by the interconnected pixel structures may be increased.

According to a further aspect of the present invention, an implant is provided, which comprises a photosensitive pixel array or at least one photosensitive pixel structure. As a photosensitive pixel structure according to a preferred embodiment of the present invention comprises an electrode suitable to stimulate living tissue or cells, the implant, as well, comprises at least one stimulating electrode. That electrode may be adapted to provide an electrical stimulation pulse generated by photoelectric generation. To achieve this, the electrode or electrodes may be connected to the photosensitive area, i.e. the diode, of the respective pixel structure or structures. In response to light incident on the pixel structure, an electric charge may be generated in the pixel structure, and, eventually, on the electrode associated with the pixel structure.

In an advantageous embodiment, the second material layer is provided adjacent to the first material layer.

Preferably, between the second material layer and the first material layer there is arranged an adhesive layer having a thickness of preferably 5 nm to 50 nm, more preferably 10 nm to 30 nm, most preferred about 20 nm+/−5 nm and which is preferably formed of titanium.

By providing a photosensitive pixel array or pixel structure, the implant is thus rendered a photosensitive implant, which may provide electrical stimulation or energy supply when implanted. In particular, the photosensitive implant may provide electrical stimulation to living tissue, such as neural tissue, or cells, being contacted by or situated in the proximity of the respective electrode. In particular, the implant, for instance a retinal implant, may allow electrical stimulation of tissue, in particular retinal tissue of an eye of a subject causing a visual sensation. That way, the implant may enable to at least partially restore vision to a patient.

In preferred embodiments, the implant is a subretinal implant. That allows to implant the implant within the eye of a patient, i.e. subretinally, in order to bypass any damaged tissue of the retina. Consequently, the electrical impulses may be generated in closer proximity to the sensitive neural cells which are still functional in the retina.

According to yet another aspect of the present invention, a method to provide a pixel structure, and, eventually, a pixel array or an implant according to one of the aspects of the present invention comprises as a first step the provision of a substrate. The substrate is adapted to absorb light. Preferably, the substrate is adapted to absorb light of at least one predetermined wavelength. That wavelength may, in particular be from the near infrared region, e.g., a wavelength above 780 nm. The substrate may also be adapted to absorb light of a plurality of predetermined wavelengths or one or more predetermined wavelength ranges. On the substrate, in a further step, at least one photosensitive diode area is provided, preferably on a front surface of the substrate. The photosensitive diode array is adapted to generate a charge in response to light absorption in the substrate of the pixel structure. Further, in one step, which may be subsequent or in advance to the above indicated steps, on a back-surface of the substrate, a first material layer is provided. That first material layer comprises at least a reflective material layer, which is adapted to reflect light, which was transmitted through the substrate to the first material layer, back toward the substrate.

The wavelength of the incident light, which shall be absorbed by the pixel structure, depending on the specific application, may also be from the visible, the ultraviolet or the far infrared region. However, for applications in an implant, wavelength from the near infrared as set out above are preferred.

In some embodiments of the present invention, the first material layer is provided by ion-implantation and/or the first material layer is thermally grown from the substrate. In particular, the buried oxide layer may be thermally grown from the substrate layer. That may increase an efficiency of a photodiode associated with the substrate by reducing surface recombination of minority carriers.

A second material layer may be provided at least on a surface of the first material layer facing away from the substrate. That second layer may in particular be a layer to improve or provide a hermetic sealing of that surface. That second material layer may therefore be provided on the surface of the first material layer facing away from the substrate only. The second material layer may, however, also at least partially enclose further portions of the substrate, such as side sections or edges and/or the top surface of the substrate or the entire pixel structure. In particular in a case where a pixel array is provided, the second material layer may enclose the pixel structure at least partially or may enclose the entire pixel structure.

BRIEF DESCRIPTION OF THE DRAWINGS

Further details, preferred embodiments and advantages of the present invention will be found in the following description with reference to the drawings, in which.

DETAILED DESCRIPTION OF THE INVENTION

Figure 1:
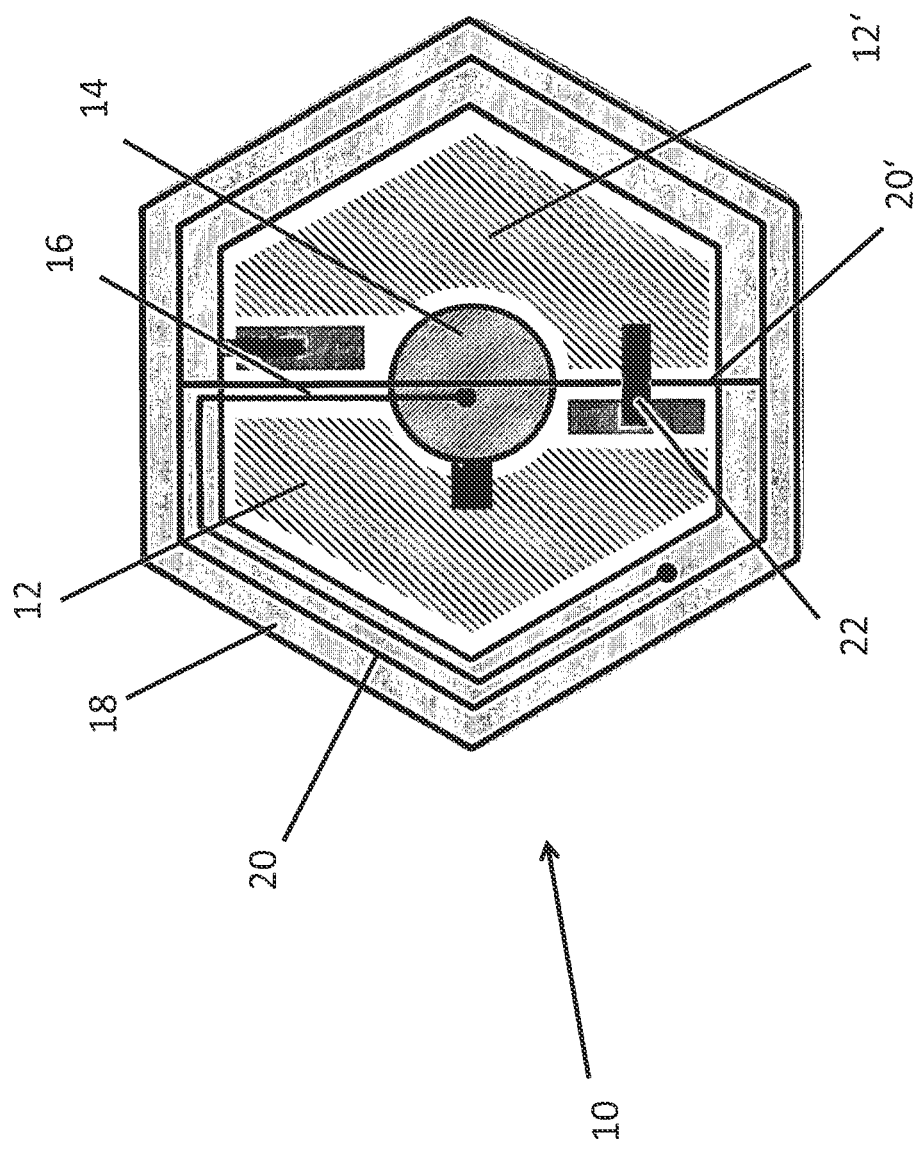
FIG. 1 is an example of a photosensitive pixel with an electrode according to one embodiment of the present invention.

FIG. 1 shows an exemplified photosensitive pixel structure 10. The photosensitive pixel structure 10, in the following also referred to as a pixel, comprises two photosensitive diodes 12, 12', a central electrode 14 and a resistor 16. At an outer periphery of the pixel structure 10, a counter electrode 18 is provided, which is also often referred to as return electrode. The counter electrode 18 can be placed on each individual pixel structure 10, for instance at the periphery of each pixel structure 10, as shown in FIG. 1. That means, the return electrode is local and in-between the different central electrodes of an array 1 of pixel structures. This is typically also referred to as a "bipolar" configuration.

For such a bipolar arrangement, two configurations are possible. The return electrodes may be disconnected from one another. That means, pixels in that case are completely independent from one another. Alternatively, all or groups of return electrodes of individual pixel structures or groups of pixel structures may be connected together, in order to effectively creating a sort of grid-like structure. Such a structure may, for instance, comprise a plurality of hexagonal pixels, which may extend over a whole pixel array 1. Examples for such pixel arrays are displayed in FIG. 3.

As a further alternative, a central return electrode (not shown) may be placed separate from the pixel structure 10, for instance at a position on a pixel array remote from the pixel structure. Such a central return electrode may in particular be provided at a remote location on the implant. Such a configuration may also be referred to as a monopolar configuration. It is to be noted that the return electrode does not necessarily have to be in a geometrical centre of the implant. Further, it is possible that a plurality of such central return electrodes are distributed over the implant or the pixel array. It will be understood that the present invention may be suitably used for either of these configurations.

Figure 3:
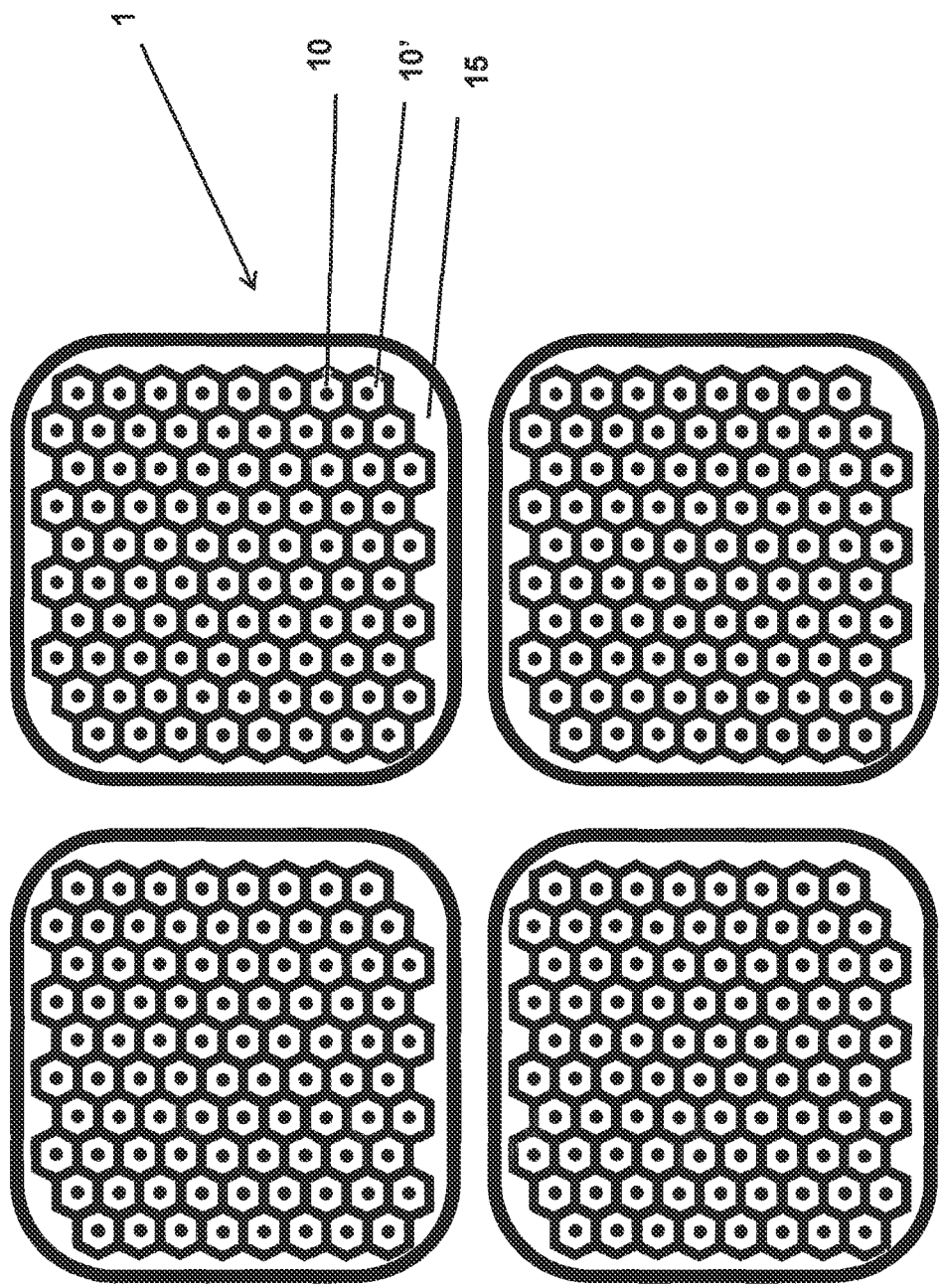
FIG. 3 displays an electrode array according to an embodiment of the present invention.

The pixel structure 10 in the embodiment of FIG. 1 has a generally symmetric hexagonal shape. That hexagonal shape is defined by trenches 20 arranged around the pixel structure and electrically isolating the pixel structure from adjacent structures Adjacent to each of the sides of that hexagon of the embodiment shown, further pixels 10' may be provided. An example for an embodiment of a pixel array 1 of pixels 10, also referred to as an electrode array in the context of the present invention, is shown in FIG. 3. In alternative embodiments, the shape of the individual pixels may also differ. For example, the pixels may have an octagonal or rectangular shape. The pixels may also have circular or diamond shape or any other, even arbitrary, shape, without departing from the scope of protection of the present invention.

Individual pixels are separated from each other by means of the trenches 20. A trench 20 comprises an electrically isolating material. Individual, adjacent pixels 10, 10' preferably are electrically isolated from one another. The counter electrode 18 as shown in the embodiment of FIG. 1 is arranged along the extension of the trench 20 surrounding the periphery of active area of the pixel 10 thus with the same, here hexagonal, contour. A cross section through a pixel structure 10' with an adjacent pixel structure 10' is shown FIG. 2.

The two diodes 12, 12' according to the embodiment of FIG. 1 are arranged inscribed within the area of the hexagonal pixel shape. Preferably, the diodes 12, 12' are symmetrically arranged. Between the diodes 12, 12', an isolating trench 20' is provided. The isolating trench 20' between the diodes 12, 12' generally has the same properties as the isolating trench 20. The different diodes 12, 12' of the pixel 10 are therefore basically electrically isolated from one another. It is to be understood that despite trenches 20' arranged within the pixel, i.e. in a substrate 15 of the photosensitive element, electrical contact between objects separated and isolated by trenches 20, 20' may still be established. In the embodiment according to FIG. 1, for instance, the diodes 12, 12' are connected by an electrical contact 22. As will be further detailed with respect to FIG. 4, the diodes 12, 12', that way, are serially connected with respect to one another in the embodiment according to FIG. 1.

The diodes 12, 12' represent in the projection view of the embodiment according to FIG. 1 a photosensitive area of the pixel 10. In that embodiment, the surface area, i.e. the photosensitive area, of the diodes 12, 12' is essentially symmetric around a symmetry axis of the pixel 10. In the embodiment of FIG. 1 such a symmetry axis may for instance coincide with the trench 20' separating the diodes 12, 12' of the pixel 10. In other embodiments, the number of diodes may be different. In particular, there may be only one diode 12 provided. That would allow to increase the photosensitive area of the pixel, as no trenches 20' had to be provided to separate individual diodes within the pixel 10. In further embodiments, three diodes or more than three diodes may be provided in one pixel. If more than two diodes are provided in a pixel 10, the individual diodes may also be serially connected with one another, as already discussed for a two-diode pixel structure above.

As may be further seen in FIG. 1, in the centre of the pixel structure 10, an electrode 14 is provided. Due to its central position, that electrode 14 is also referred to as central electrode. Further, as that electrode typically is used for stimulation, that electrode is also referred to as stimulating electrode. The stimulating electrode 14 in the shown embodiment is provided having a circular shape. The electrode may also have different shapes, such as a shape similar to the shape of the return electrode 18 or the trench 20 reflecting the contour of the pixel 10. The circular shape of the presently shown embodiment was chosen such that the electrical field from the stimulating electrode 14 may be homogenous. Depending on the intended application, the shape may also include such shapes which allow less homogenous, locally enhanced field distributions.

According to some embodiments of the present invention, the electrode 14 of the pixel 10 shall be adapted for stimulation of surrounding tissue, preferably neural tissue, in particular neural tissue of a retina in vivo. Typically, the electrode comprises platinum, iridium oxide and/or titanium nitride. Alternatively, iridium, platinum iridium, doped diamond or diamond-like carbon or PEDOT:PSS, or other known materials may be used as electrode material. The preferred structure of the electrode material may in particular be a highly porous structure, such as a porous or fractal TiN, a platinum structure or SIROF. Such structures are known and found to be described to be, e.g., "black platinum" or "porous platinum". The thickness of the electrodes may vary from about 100 nm to 3 µm. It is, however, also possible to have an electrode thickness up to or above 10 µm as well, or below 100 nm.

In the embodiment as shown in FIG. 1, the return electrode 18 is provided as an elongate electrode surrounding the pixel and following the contour of the pixels periphery, i.e., in the shown embodiment, the run of the trench 20. In alternative embodiments, the return electrode may also comprise a plurality of electrodes, which are distributed around the pixel structure 10 and around the stimulating electrode 14 in regular or arbitrary distribution. This may in particular be exerted at a peripheral portion of an electrode array 1.

Further, between the stimulating electrode 14 and the counter electrode 18, the resistor 16, also referred to as a shunt resistor, is arranged. That resistor 16 according to the embodiment shown in FIG. 1 of the present invention, is electrically connected to the stimulating electrode 14 and to the counter electrode 18.

As indicated above, a plurality of diodes, for instance two or three diodes, within one pixel 10, may be provided, if the voltage, as response to a light signal received, needs to be increased. The diodes may for such cases be serially connected, wherein the voltage of a number N of diodes is the factor N higher than the voltage created by one diode only. On the other hand, an increased number of diodes means that fewer light may be collected by each diode, per pixel. The electrical current created by each of those diodes connected in series may therefore be significantly lower when having a plurality of diodes compared to having only one or a few diodes. Typically, the current in a circuit with N diodes is N times less than the current in a circuit with one diode. It is therefore a matter of choice, which of the parameters, i.e., current or voltage, is more desirable for an individual application. In the specific case of neural stimulation, the required stimulation parameters may depend on the tissue and/or the individual cells, in particular neural cells, to be excited, the position of an implant and even individual specifics of a patient, possibly age, state of disease and general physiological condition.

Figure 2:
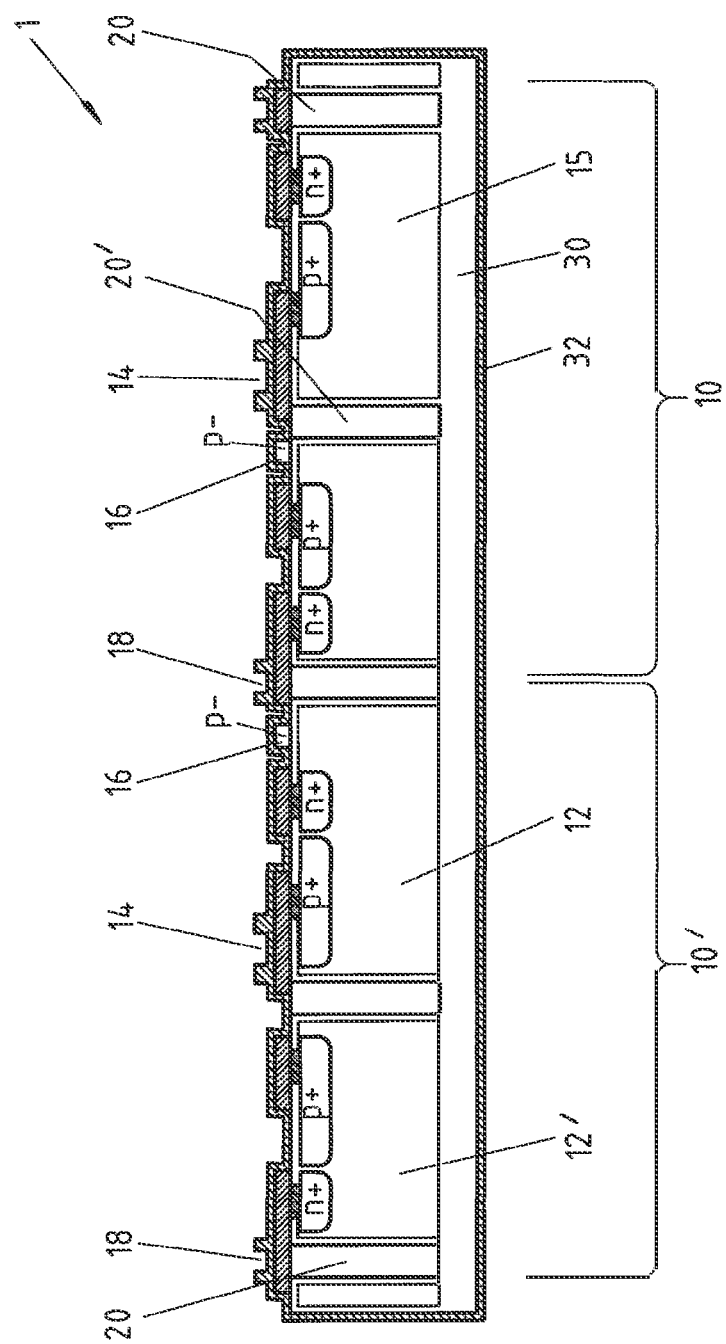
FIG. 2 is a schematic cross-sectional view of a semiconductor structure with two adjacent pixels according to an embodiment of the invention.

In order to increase the current generated, thus, it is therefore desired to increase the light absorption in the substrate. FIG. 2 shows a sectional side view of a portion of an electrode array 1, showing two adjacent pixels 10, 10'. The pixels 10, 10' correspond to the pixels of the pixel structure according to the embodiment as shown in FIG. 1, having two diodes 12, 12'. The same layer structure as shown in FIG. 1 for a two-diode pixel may essentially also be provided for a one-diode or three-diode pixel, analogously.

Further, in FIG. 2, a first material layer 30 is shown. That material layer 30 may be formed as an integral part of the substrate 15, as in the case for the embodiment shown in FIG. 2. Alternatively, the first material layer may at least partially be an integral part of the substrate 15, or may be a layer deposited on the substrate 15.

The first material layer 30 is provided adjacent and subsequent to a back surface of the substrate 15. The first material layer 30 may, for instance, comprise a buried oxide layer, in particular an $SiO_2$ layer. The buried oxide layer may be thermally grown on the substrate 15. The substrate layer preferably comprises silicon. In addition, the first material layer 30 may be a stacked layer comprising, subsequent to the buried oxide layer, a metal layer, such as an aluminium or titanium layer.

In the embodiment according to FIG. 2, a second material layer 32 adjacent to the first material layer 30 is provided on a surface of the first material layer 30 which faces away from the substrate 15. The second material layer 32 may comprise a metal, such as aluminium or titanium, or a stack of metals. Preferably, the outermost layer of the pixel structure 10 at least on the back surface of the substrate 15, i.e., the outermost layer of the second material layer 32, comprises a material which allows a hermetic sealing of the back surface of the substrate 15, or of the back surface of the substrate and at least a part of the side portion of the pixel structure. That way, as may be seen in FIG. 2, the edge of the pixel structure may be hermetically sealed and the pixel structure may be protected from corrosion or decay due to environmental effects. In case that an entire pixel array 1, as shown in FIG. 3, or an implant shall be provided, the hermetic sealing may be provided on the outermost layer, edge and/or side portion of that pixel array 1.

It will be understood that the definition as a "layer", in particular with respect to the first material layer 30, is used in order to better describe the characteristics of the pixel structure 10. However, as a consequence of the methods used to produce the pixel structure 10 according to the invention, the individual layers such as the substrate 15, the first material layer 30 or the second material layer 32 may be integrated into another. The Methods used to provide the layer structure according to the present invention may for instance include thermal growing, ion deposition, electrochemical deposition, physical vapour deposition, such as sputtering and electron beam evaporation, or other methods. Consequently, a pixel structure produced accordingly may actually not appear to have a layer appearance, or display separable layers, while, functionally, layers, e.g. according to embodiments of the present invention, are in fact provided therein. According to a special embodiment, at least two "layers" can be separated by one adhesive layer 33. Said adhesive layer 33 may have a thickness of preferably 5 nm to 50 nm, more preferably 10 nm to 30 nm, most preferred about 20 nm+/−5 nm. The adhesive layer 33 may be formed of titanium which has good adhesive properties. Preferably, there is no adhesive layer 33 between layer 15 and 30 when the first material layer 30 comprises buried oxide layer thermally grown on the substrate 15.

FIG. 3 shows an array of pixel structures 10, 10', i.e., a pixel array 1. In the embodiment shown in FIG. 3, the pixel array 1 is an array of pixel structures 10, 10' wherein each of the pixel structures 10. 10' comprise a stimulating electrode 14 configured to stimulate cells or living tissue. Therefore, the pixel array 1 may also be referred to as an electrode array. The size of the individual pixel structures 10, 10' in the array 1 may differ and can thus be tuned to different applications, without departing from the scope of the present invention. In the array 1 displayed in FIG. 3, the individual pixels 10, 10' are hexagonally formed, which allows a space efficient distribution on the substrate 15. That way, the space available for light sensitive regions on the substrate 15 and within an array 1 may be increased and ideally maximized. A pixel array 1 as shown in FIG. 3 may for instance be used in an implant in order to stimulate cells or living tissue, in particular living tissue, such as neural tissue, or neural cells.

According to embodiments of the present invention, not shown in FIG. 3, first and/or the second material layer may be formed around the back surface of the array, i.e. the surface build by the plurality of back surfaces of the individual pixel structures. In addition, the first and/or second material layer may be formed around an edge of the array 1, in order to provide a sealing or protection to the array.

Figure 4:
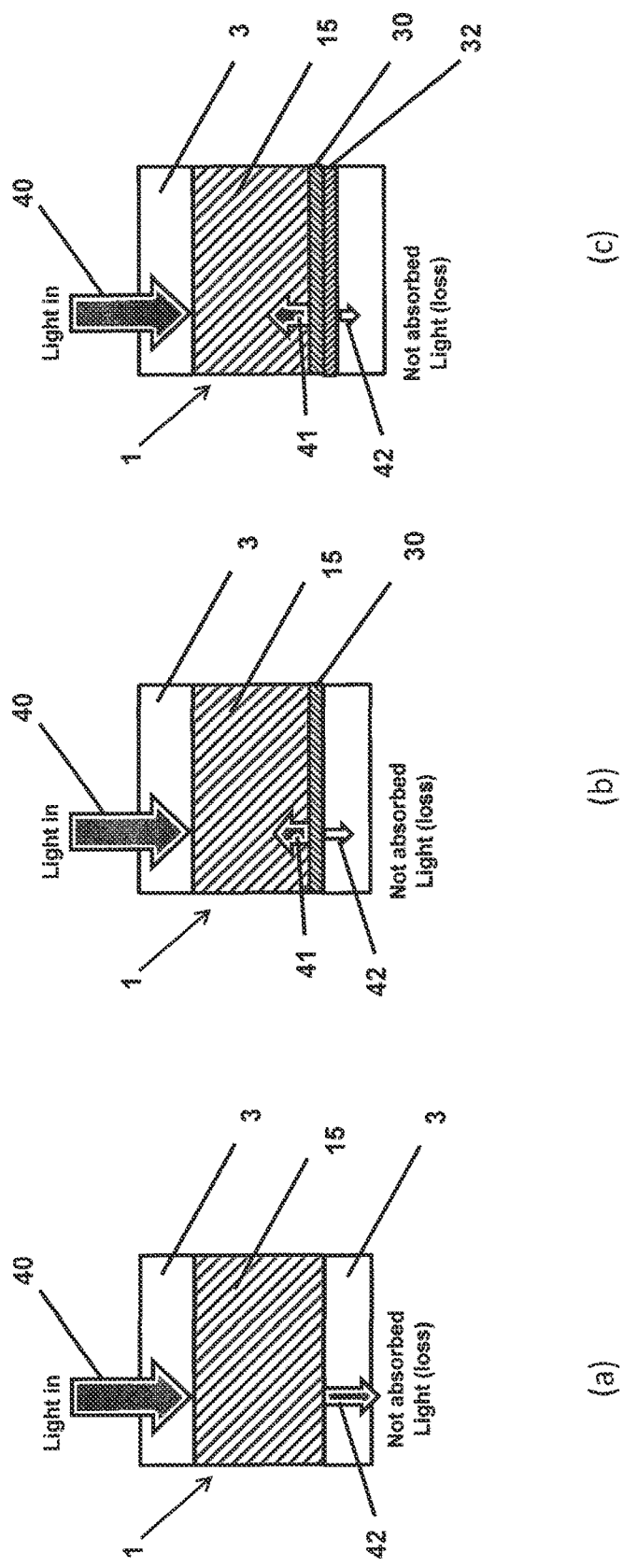
FIG. 4 shows a schematic cross section of (a) a substrate embedded in a retina; (b) a photosensitive pixel structure according to an embodiment of the present invention embedded in a retina; and (c) a photosensitive pixel structure according to another embodiment of the present invention embedded in a retina and (d) a photosensitive pixel structure according to another embodiment of the present invention embedded in a retina
Figure 4:
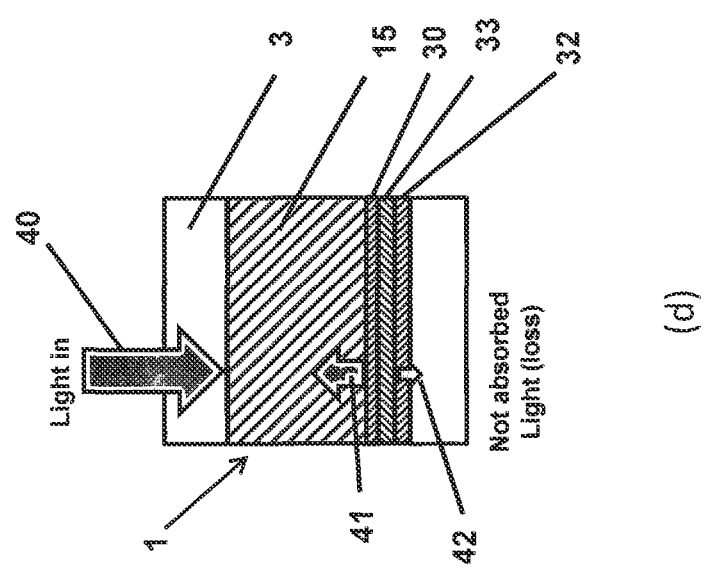

FIG. 4 (a) shows a schematic cross section of a pixel array 1, which is embedded in tissue, here for instance in a retina 3. The pixel array 1 is represented by the substrate 15, wherein any surface structures, such as diodes or electrodes, are not displayed in the figure.

Commonly, when implanting a pixel array 1, or an implant, into a retina 3, the substrate is arranged such that light, represented by the arrow 40 in FIG. 4 (a), which is incident on the eye may traverse the retina and be incident on a front surface of the substrate 15. From the front surface of the substrate 15, the light enters and traverses the substrate 15 where it is absorbed depending on the material of the substrate 15, the wavelength of the incident light, and other factors. The substrate 15 used typically comprises or consists of silicon.

For a typical thickness of 30 µm of silicon substrate, and at a wavelength of 830 nm of the incident light, about 85% of the incident light is absorbed. At a wavelength of 880 nm, 68% of the incident light are absorbed and at a wavelength of 915 nm, only about 53% of the incident light are absorbed. If the substrate is to be used in an implant in order to restore vision, the stimulation of a pixel structure 10 comprising the substrate 15 needs to be in the infrared or near-infrared region of the spectrum, such that residual vision of the retina is not disturbed. The light, which is not absorbed in the substrate 15 is incident on the back surface of the substrate 15. At the back surface of the substrate 15, due to the intrinsic material properties and the laws of reflection, about 21% of the light is reflected back into substrate (not shown in FIG. 4 (a)), while the bigger part of the light exits the substrate 15 as indicated with arrow 42 in FIG. 4 (a) and is lost.

As displayed in FIG. 4 (b), according to an embodiment of the present invention, on the back surface of the substrate 15 a first material layer 30 is provided adjacent to the substrate 15. That first material layer 30 may also be a stack of materials. The first material layer 30 comprises at least a reflective material layer, which increases the reflectivity at the back surface of the substrate. Thereby, an increased fraction of the light initially transmitted through the substrate 15 without being absorbed may be reflected back into the substrate 15, as indicated with the arrow 41 in FIG. 4 (b). Accordingly, less light will be lost for a photo-electrical reaction.

FIG. 4 (c) displays a further embodiment of the present invention, according to which a second material layer 32 is provided adjacent to the first material layer 30. Such a second material layer 32 may allow a further increase in reflectivity at the back surface of the substrate 15. That may further increase the absorption rate. The second material layer 32 may be a material which allows a hermetic sealing, such as titanium. Thereby, the reflectivity at the back surface may be increased, while, at the same time, hermeticity of the pixel structure 10 or the entire pixel array 1 or implant may be enabled. Further materials to provide a hermetic cover layer, coating or housing may be ceramic layers, such as aluminium oxide, silicon carbide or others.

FIG. 4 (d) displays a further embodiment of the present invention, according to which a second material layer 32 is provided adjacent to the first material layer 30 similar to the embodiment of FIG. 4 (c). Again, the second material layer 32 may allow a further increase in reflectivity at the back surface of the substrate 15. The first material layer 30 may be formed of silicon dioxide, while the second material layer 32 may be formed of Aluminium, having a thickness of 100 nm or more, or may be formed by a stack of Aluminium and Titanium, having a thickness of 100 nm or more each. Between the second material layer 32 of Aluminium, or Aluminium and Titanium, and the first material layer 30 of silicon dioxide there is arranged an adhesive layer 33 having a thickness of preferably 5 nm to 50 nm, more preferably 10 nm to 30 nm, most preferred about 20 nm+/−5 nm. The adhesive layer 33 may be formed of titanium which has good adhesive properties.

Figure 5:
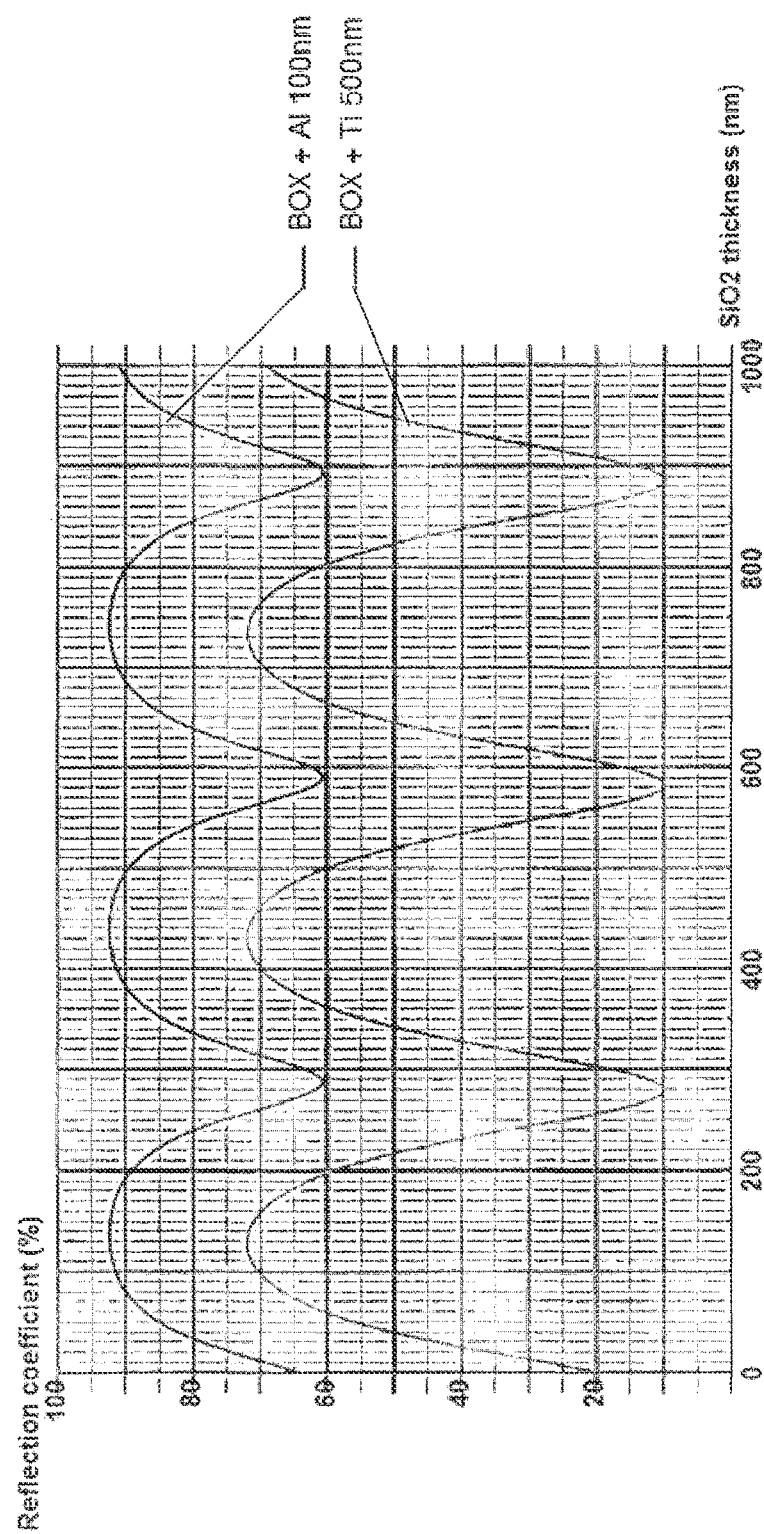
FIG. 5 shows a diagram representing the reflection coefficient in dependence from the thickness of a buried oxide layer on a back surface of a pixel structure according to an embodiment of the present invention.

FIG. 5 shows a graph representing the reflection coefficient versus the thickness of a buried oxide layer of a stacked first material comprising the buried oxide layer and an aluminium layer (upper curve) and a buried oxide layer and a titanium layer (lower curve). It will be noted that the reflectivity of the BOX/Al-stack significantly surpasses that of the BOX/Ti-stack at and around a thickness of the buried oxide layer of 130 nm, 430 nm or 130 nm plus multiples of 300 nm. Further, the slope of the curve of the BOX/Al-stack is flatter in the range of that preferred thicknesses of 130 nm, 430 nm or 130 nm plus multiples of 300 nm of the buried oxide layer than the curve of the BOX/Ti-layer.

The graphs displayed in FIG. 5 are based on simulation results of a substrate 15 consisting of silicon, a first material layer 30 stacked of SiO$_2$ and aluminium or titanium, and a subsequent retinal layer 3. Indices of refraction for that simulation were assumed to be 3.66 for Si, 1.4525 for SiO$_2$, 2.58+8.21 I for Al, 3.06+3.305 I for Ti, and 1.36 for the retinal tissue at a wavelength of 880 nm. While these data represent specific embodiments of the present invention, similar or same conclusions, in particular to the BOX-thickness, may be drawn also for different wavelength or material properties. These examples shall not be construed to limit the scope of the present invention to the specific examples. Rather, various implementations with different materials, material thicknesses, layer numbers, reflective indices and so on may be applied within the scope of the present invention.

It is further to be understood that according to the present invention, the thickness of the BOX-layer may be varied to thicknesses higher or lower than the indicated preferred thickness of around 130 nm, 430 nm or 130 nm plus multiples of 300 nm.

The invention claimed is:

1. Photosensitive pixel structure comprising:
   a substrate with a front surface and a back surface and at least one photosensitive diode provided on one of the front surface or the back surface of the substrate;
   a first material layer provided at least partially on the back surface of the substrate, wherein the first material layer comprises a reflective layer; and
   a second material layer provided on at least a part of a back surface of the first material layer and configured to hermetically cover and hermetically seal at least the first material layer and/or the back surface of the substrate and form an outer layer of the photosensitive pixel structure, the second material layer comprising titanium and/or ceramic.

2. Photosensitive pixel structure according to claim 1, wherein the substrate comprises a material which is adapted to absorb light of a predetermined wavelength or wavelength range.

3. Photosensitive pixel structure according to either one of claim 1 or 2, characterized in that the first material layer on the back surface of the substrate comprises a layer of buried oxide or the first material layer comprises a layer of metal.

4. Photosensitive pixel structure according to claim 3, characterized in that the first material layer is formed as an integral part of the substrate.

5. Photosensitive pixel structure according to claim 3, characterized in that the first and/or the second material layer comprises titanium and the titanium layer has a thickness selected from not less than 100 nm.

6. Photosensitive pixel structure according to claim 5, wherein, in a case that a stack of titanium and buried oxide layer is used as a first material layer, the thickness of the buried oxide layer is in a range of about 65 nm and 210 nm, or, in a case that a stack of aluminium and buried oxide layer is used as a first material layer, the thickness of the buried oxide layer is in the range selected from 90 nm to 170 nm plus any multiple of 300 nm.

7. Photosensitive pixel structure according to claim 1, characterized in that the first material layer comprises a layer of buried oxide, and a layer of aluminium, wherein the layer of buried oxide is sandwiched between the substrate and the layer of aluminium.

8. Photosensitive pixel structure according to claim 1, characterized in that the second material layer consists of titanium and/or a ceramic layer.

9. Photosensitive pixel array comprising a plurality of pixel structures according to claim 1, wherein the plurality of pixel structures is arranged in an array.

10. Implant with a photosensitive pixel array according to claim 9, wherein the implant further comprises at least one electrode, which is adapted to provide an electrical stimulation pulse generated by photoelectric generation in the pixel structure or pixel array.

11. Photosensitive pixel array comprising a plurality of pixel structures according to claim 1, wherein the second material layer is provided adjacent to the first material layer.

12. Implant with a photosensitive pixel structure according to claim 1, wherein the implant further comprises at least one electrode, which is adapted to provide an electrical stimulation pulse generated by photoelectric generation in the pixel structure.

13. Implant according to claim 12, wherein the implant is a retinal implant or a subretinal implant.

14. Method for providing a pixel structure according to claim 1, characterized in that the method comprises the steps of:
   providing the substrate adapted to absorb light of at least one predetermined wavelength,
   providing on the front surface of the substrate the photosensitive diode,
   providing on the back surface of the substrate the first material layer which comprises at least a reflective material layer, which is adapted to reflect light transmitted through the substrate to the first material layer back toward the substrate.

15. Method according to claim 14, characterized in that the first material layer is provided by ion-implantation and/or the first material layer is thermally grown from the substrate.

16. Method according to of claim 15, characterized in that the second material layer is provided at least on a surface of the first material layer facing away from the substrate.

17. Method according to claim 14, characterized in that the second material layer is provided at least on a surface of the first material layer facing away from the substrate.

18. Implant with a photosensitive pixel structure according to claim 1, wherein the second material layer comprises ceramic.

* * * * *